(12) United States Patent
Zhou et al.

(10) Patent No.: US 11,504,018 B2
(45) Date of Patent: Nov. 22, 2022

(54) ELECTRODE MULTIPLEXED PHYSIOLOGICAL PARAMETER MONITORING FINGER RING

(71) Applicant: Hangzhou Megasens Technologies Co., Ltd., Zhejiang (CN)

(72) Inventors: Congcong Zhou, Zhejiang (CN); Jun Hu, Zhejiang (CN); Haiquan Yuan, Zhejiang (CN)

(73) Assignee: Hangzhou Megasens Technologies Co., Ltd., Zhejiang (CN)

( * ) Notice: Subject to any disclaimer, the term of this patent is extended or adjusted under 35 U.S.C. 154(b) by 0 days.

(21) Appl. No.: 16/613,581

(22) PCT Filed: Dec. 7, 2018

(86) PCT No.: PCT/CN2018/119855
§ 371 (c)(1),
(2) Date: Nov. 14, 2019

(87) PCT Pub. No.: WO2019/184440
PCT Pub. Date: Oct. 3, 2019

(65) Prior Publication Data
US 2021/0321893 A1    Oct. 21, 2021

(30) Foreign Application Priority Data

Mar. 29, 2018   (CN) .......................... 201810269936.2

(51) Int. Cl.
*A61B 5/024*       (2006.01)
*A61B 5/318*       (2021.01)
(Continued)

(52) U.S. Cl.
CPC ........ *A61B 5/02438* (2013.01); *A61B 5/0531* (2013.01); *A61B 5/28* (2021.01);
(Continued)

(58) Field of Classification Search
CPC ..... A61B 5/02438; A61B 5/0531; A61B 5/28; A61B 5/318; A61B 5/7225;
(Continued)

(56) References Cited

U.S. PATENT DOCUMENTS

| 9,685,802 | B1* | 6/2017 | Mirov ................... H02J 7/0044 |
| 2013/0116577 | A1 | 5/2013 | Yazicioglu et al. |
| 2017/0105646 | A1* | 4/2017 | Bryenton ............. A61B 5/6828 |

FOREIGN PATENT DOCUMENTS

| CN | 1692874 A | 11/2005 |
| CN | 102499636 A | 6/2012 |

(Continued)

OTHER PUBLICATIONS

R.S. Sedha, "Textbook of Applied Electronics" 2008, International Book Distributing Co, pp. 746-763 (Year: 2008).*

*Primary Examiner* — Brian T Gedeon
*Assistant Examiner* — Joshua Andrew Schum-Houck
(74) *Attorney, Agent, or Firm* — Elmore Patent Law Group, P.C.; Carolyn Elmore; Joseph Zucchero

(57) ABSTRACT

An electrode multiplexing physiological parameter monitoring ring, comprising a built-in power supply (2), a microprocessor module (1), an electrocardiogram monitoring analog front end (3), a skin conductance monitoring module (4), a first electrode (6), and a second electrode (7). The microprocessor module (1) is connected to the electrocardiogram monitoring analog front end (3) and the skin conductance monitoring module (4). The first electrode (6) and the second electrode (7) are connected to the electrocardiogram monitoring analog front end (3), and the electrocardiogram monitoring analog front end (3) processes electrocardiogram signals collected by the first electrode (6) and the second electrode (7). The first electrode (6) and the second electrode (7) are further connected to the skin conductance monitoring module (4), and the skin conductance monitoring module (4) processes skin impedance signals collected by the first electrode (6) and the second electrode (7). A coupling manner in which the first electrode (6) and the second electrode (7) are coupled to the electrocardiogram monitoring analog front end (3) is direct current coupling or alter- (Continued)

nating current coupling, and is opposite to a coupling manner in which the first electrode (6) and the second electrode (7) are coupled to the skin conductance monitoring module (4). By means of the electrode multiplexing physiological parameter monitoring ring, electrocardiogram monitoring, heart rate monitoring, and skin conductance monitoring are implemented through only two electrodes, so that the number of electrodes is reduced, and system design is simplified.

7 Claims, 3 Drawing Sheets

(51) Int. Cl.
*A61B 5/28* (2021.01)
*A61B 5/0531* (2021.01)
*A61B 5/00* (2006.01)

(52) U.S. Cl.
CPC ............ *A61B 5/318* (2021.01); *A61B 5/7225* (2013.01); *A61B 2560/0214* (2013.01)

(58) Field of Classification Search
CPC . A61B 2560/0214; A61B 5/282; A61B 5/308; A61B 5/02444; A61B 5/304; A61B 5/6826
See application file for complete search history.

(56) References Cited

FOREIGN PATENT DOCUMENTS

| | | |
|---|---|---|
| CN | 103908241 A | 7/2014 |
| CN | 105232034 A | 1/2016 |
| CN | 107205676 A | 9/2017 |
| CN | 207150557 U | 3/2018 |
| WO | 2013038285 A1 | 3/2013 |

\* cited by examiner

ELECTRODE MULTIPLEXED PHYSIOLOGICAL PARAMETER MONITORING FINGER RING

RELATED APPLICATIONS

This application is a US National stage entry of International Application No. PCT/CN2018/119855, which designated the United States and was filed on Dec. 7, 2018, published in Chinese which claims priority to Chinese Application No. 201810269936.2, filed Mar. 29, 2018. The entire teachings of the above applications are incorporated herein by reference.

TECHNICAL FIELD

The present invention relates to the field of health medical device, and specifically, to an electrode multiplexing physiological parameter monitoring ring.

BACKGROUND

It is very important for long-term physiological assessment to record human physiological parameters and skin impedance signals in real time. With the development of medical monitoring technology, wearable devices have become more and more widely used. Generally, existing wearable devices require at least two electrodes to collect electrocardiogram signals for electrocardiogram monitoring and heart rate monitoring. In addition, in order to perform skin conductance monitoring, four additional electrodes which are different from the electrodes for collecting the electrocardiogram signals are employed in the existing wearable devices to collect skin impedance signals, wherein a pair of electrodes is used as an excitation source to generate a signal, and another pair of electrodes is used as a collection end to collect a corresponding voltage signal. It can be seen that the existing wearable device has a large number of electrodes, high redundancy, complicated system design, and cannot implement device miniaturization.

SUMMARY

To solve some or all of the above-mentioned problems, the present invention provides an electrode multiplexing physiological parameter monitoring ring.

Embodiments of the present invention disclose an electrode multiplexing physiological parameter monitoring ring, including a built-in power supply, a microprocessor module, an electrocardiogram monitoring analog front end, a skin conductance monitoring module, a first electrode, and a second electrode. The microprocessor module is connected to the electrocardiogram monitoring analog front end and the skin conductance monitoring module.

The first electrode and the second electrode are separately connected to the electrocardiogram monitoring analog front end, and the electrocardiogram monitoring analog front end processes electrocardiogram signals collected by the first electrode and the second electrode.

The first electrode and the second electrode are further separately connected to the skin conductance monitoring module, and the skin conductance monitoring module processes skin impendence signals collected by the first electrode and the second electrode.

A coupling manner in which the first electrode and the second electrode are coupled to the electrocardiogram monitoring analog front end is direct current coupling or alternating current coupling, and is opposite to a coupling manner in which the first electrode and the second electrode are coupled to the skin conductance monitoring module.

In an example, the ring further includes a power supply management module connected to the microprocessor module. The first electrode and the second electrode are separately connected to the built-in power supply through the power supply management module.

The power supply management module is configured to: when the first electrode and the second electrode are in contact with skin, form an open circuit between the first electrode and the built-in power supply, and when the first electrode and the second electrode are connected to an external charger, form a closed-circuit between the first electrode and the built-in power supply.

The microprocessor module is configured to: when the closed-circuit is formed between the first electrode and the built-in power supply, make the electrocardiogram monitoring analog front end and the skin conductance monitoring module stop working.

In an example, the ring further includes a third electrode connected to the electrocardiogram monitoring analog front end. The electrocardiogram monitoring analog front end processes electrocardiogram signals collected by the first electrode, the second electrode, and the third electrode. The third electrode is coupled to the electrocardiogram monitoring analog front end in a manner of direct current coupling.

In an example, the skin conductance monitoring module includes a signal excitation module and a signal processing module.

In an example, the signal excitation module includes a current source, a first resistor, a second resistor, a first capacitor, and a second capacitor. One end of the first resistor is connected to the current source, the other end of the first resistor is connected to the first capacitor, and the other end of the first capacitor is connected to the first electrode. One end of the second capacitor is connected to the current source, the other end of the second capacitor is connected to the second capacitor, and the other end of the second capacitor is connected to the second electrode.

In an example, the signal excitation module generates an alternating current with a frequency higher than 32 kHz and amplitude lower than 100 μA.

In an example, the signal processing module includes a third capacitor, a fourth capacitor, a band-pass filter, and a low-pass filter. One end of the third capacitor is connected to the first electrode, the other end of the third capacitor is connected to the band-pass filter, and the other end of the band-pass filter is connected to the low-pass filter. One end of the fourth capacitor is connected to the second electrode, and the other end of the fourth capacitor is connected to the band-pass filter.

In an example, the power supply management module includes a third resistor, a fourth resistor, a bias voltage, and a voltage control switch. One end of the third resistor is connected to the first electrode and the voltage control switch, the other end of the third resistor is connected to the fourth resistor, and the other end of the fourth resistor is connected to the bias voltage. When the first electrode is in contact with the skin, the other end of the voltage control switch is connected to a connection point of the third resistor and the fourth resistor. When the first electrode is connected to the external charger, the other end of the voltage control switch is connected to the built-in power supply.

In an example, the bias voltage is greater than 2 V and less than 3.3 V.

Comparing the embodiments of the present invention with the prior art, the main differences and effects are as follows: A first electrode and a second electrode are multiplexed, so that electrocardiogram monitoring, heart rate monitoring, and skin conductance monitoring can be implemented by using only two electrodes; and the electrocardiogram monitoring, the heart rate monitoring, and the skin conductance monitoring do not interfere with each other, because the first electrode and the second electrode are separately coupled to the electrocardiogram monitoring analog front end and the skin conductance monitoring module in different coupling manners. In addition, the physiological parameter monitoring ring in the embodiments of the present invention can reduce the number of electrodes, simplify system design, and implement device miniaturization.

Further, a charging function can be implemented by the first electrode and the second electrode, and the physiological parameter monitoring function and the charging function can be automatically switched, so that system complexity is further reduced, and lower power consumption is implemented.

Further, three electrodes are used to collect the electrocardiogram signal, so that effects of electrocardiogram monitoring and heart rate monitoring can be improved.

DESCRIPTION OF EMBODIMENTS

In the following description, numerous technical details are provided for a reader to better understand the present application. However, persons of ordinary skill in the art can understand that the technical solutions that the claims of the present application request to protect can be implemented without these technical details and various changes and modifications based on the following embodiments.

To make the objectives, technical solutions, and advantages of the embodiments of the present invention clearer, the following describes the embodiments of the present invention in detail with reference to the accompanying drawings.

Figure 1:
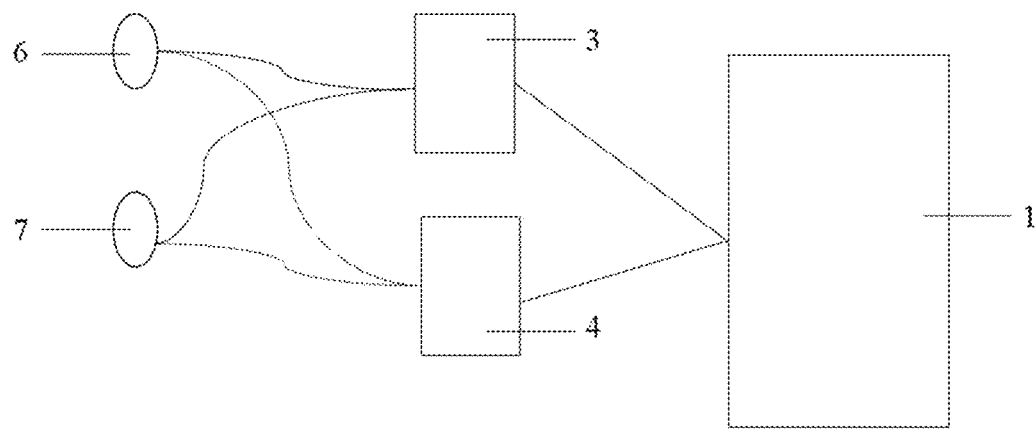
FIG. 1 is a schematic diagram of function modules of an electrode multiplexing physiological parameter monitoring ring according to an embodiment of the present invention.

FIG. 1 is a schematic diagram of function modules of an electrode multiplexing physiological parameter monitoring ring according to an embodiment of the present invention. As shown in FIG. 1, the electrode multiplexing physiological parameter monitoring ring includes a microprocessor module 1, a built-in power supply 2, an electrocardiogram monitoring analog front end 3, a skin conductance monitoring module 4, a first electrode 6, and a second electrode 2. The microprocessor module 1 is connected to the electrocardiogram monitoring analog front end 3 and the skin conductance monitoring module 4. The first electrode 6 and the second electrode 7 are separately connected to the electrocardiogram monitoring analog front end 3. The electrocardiogram monitoring analog front end 3 processes electrocardiogram signals collected by the first electrode 6 and the second electrode 7. The first electrode 6 and the second electrode 7 are further separately connected to the skin conductance monitoring module 4. The skin conductance monitoring module 4 processes skin impendence signals collected by the first electrode 6 and the second electrode 7. A coupling manner in which the first electrode 6 and the second electrode 7 are coupled to the electrocardiogram monitoring analog front end 3 is direct current coupling or alternating current coupling, and is opposite to a coupling manner in which the first electrode 6 and the electrode 7 are coupled to the skin conductance monitoring module 4. In this embodiment, the first electrode 6, the second electrode 7, and the electrocardiogram monitoring analog front end 3 constitute a single-lead electrocardiogram monitoring structure, to implement single-lead electrocardiogram monitoring and heart rate monitoring. The first electrode 6, the second electrode 7, and the skin conductance monitoring module 4 constitute a skin conductance monitoring structure to implement skin conductance monitoring. The first electrode 6 and the second electrode 7 are multiplexed, so that the physiological parameter monitoring ring of this embodiment of the present invention can implement electrocardiogram monitoring, heart rate monitoring, and skin conductance monitoring simultaneously with only two electrodes; and because the first electrode 6 and the second electrode 7 are separately coupled to the electrocardiogram monitoring front end 3 and the skin conductance monitoring module 4 in different coupling manners, the electrocardiogram monitoring, the heart rate monitoring, and the skin conductance monitoring will not interfere with each other. In addition, the physiological parameter monitoring ring in this embodiment of the present invention can reduce the number of electrodes, simplify system design, and implement device miniaturization.

The microprocessor module 1 controls electrocardiogram monitoring and skin conductance monitoring and receives and processes the signals from the electrocardiogram monitoring analog front end 3 and the skin conductance monitoring module 4. The microprocessor module 1 is connected to the electrocardiogram monitoring analog front end 3 through an SPI interface, an I2C interface, or an ADC interface. The microprocessor module 1 is connected to the skin conductance monitoring module 4 through an IO interface or the ADC interface.

The built-in power supply 2 supplies power to constituent modules inside the ring according to the needs of the system design.

The electrocardiogram monitoring analog front end 3 may be connected to the first electrode 6 and the second electrode 7 by direct current coupling, and processes (for example, amplifies or filters) the electrocardiogram signals collected by the first electrode 6 and the second electrode 7. The electrocardiogram monitoring analog front end 3 may be an AFE of ADS series of TI Company, or may be a product of ADI Company with similar functions.

Figure 2:
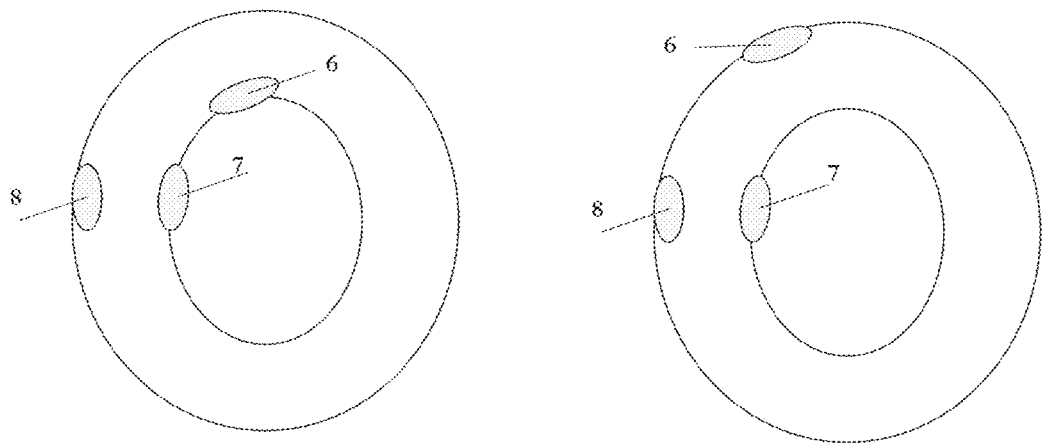
FIG. 2 is a schematic diagram of electrode distribution of an electrode multiplexing physiological parameter monitoring ring according to an embodiment of the present invention.

FIG. 2 is a schematic diagram of electrode distribution of an electrode multiplexing physiological parameter monitoring ring according to an embodiment of the present invention. As shown in FIG. 2, the first electrode 6 and the second electrode 7 may be located on the same side of the ring. Preferably, the first electrode 6 and the second electrode 7 are located on the inner side that is in contact with the skin. The first electrode 6 and the second electrode 7 can also be located in different sides of the ring. Preferably, the first electrode 6 is located on the outer side of the ring, and the second electrode 7 is located on the inner side of the ring. In addition, in order to improve the electrocardiographic monitoring effect, the electrode multiplexing physiological parameter monitoring ring preferably includes a third electrode 8 which is connected to the electrocardiographic monitoring analog front end 3 by direct current coupling. The electrocardiogram monitoring analog front end 3 processes electrocardiographic signals collected by the electrode 6, the second electrode 7, and the third electrode 8, that is, the first electrode 6, the second electrode 7, and the third electrode 8, and the electrocardiographic monitoring analog front end 3 constitute a single-lead electrocardiogram monitoring structure to implement single-lead electrocardiogram monitoring and heart rate monitoring. As shown in FIG. 2, the third electrode 8 may be located on the outer side of the ring.

Figure 3:
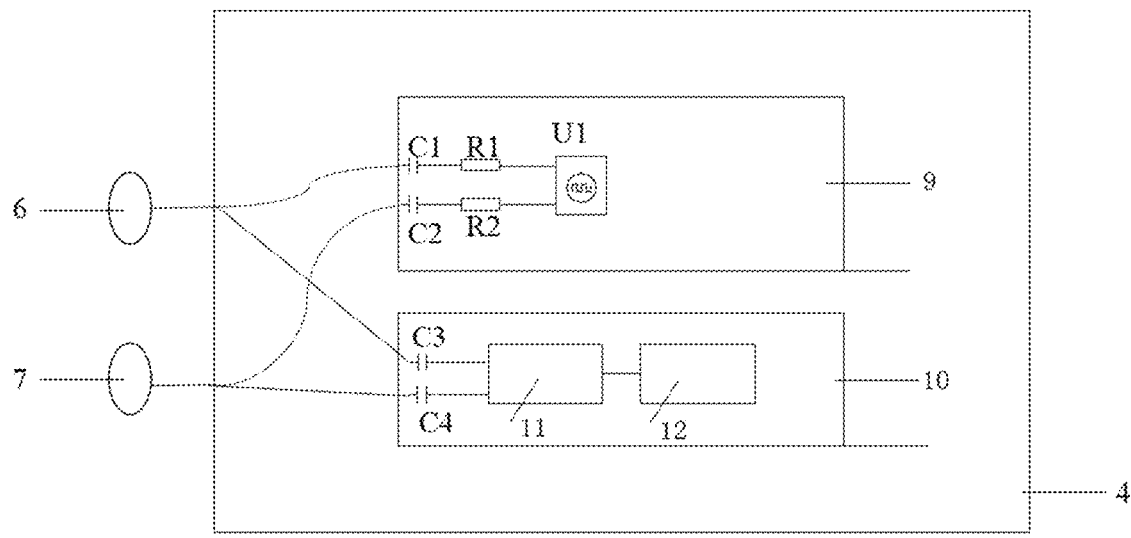
FIG. 3 is a schematic circuit diagram of a skin conductance monitoring module of an electrode multiplexing physiological parameter monitoring ring according to an embodiment of the present invention.

FIG. 3 is a schematic circuit diagram of a skin conductance monitoring module 4 of an electrode multiplexing physiological parameter monitoring ring according to an embodiment of the present invention. As shown in FIG. 3, the skin conductance monitoring module 4 includes a signal excitation module 9 and a signal processing module 10. The signal excitation module 9 is used for generating a constant current source, and the signal processing module 10 is used for collecting and demodulating a received signal. The signal excitation module 9 generates an alternating current with a frequency greater than 32 kilohertz and amplitude lower than 100 microamperes. Preferably, the alternating current generated by the signal excitation module 9 is square wave. The signal excitation module 9 includes a current source U1 for generating an alternating current, and the current source U1 is connected to the multiplexed electrode through a resistor-capacitor network. For example, the current source U1 is connected to the first electrode 6 through a resistor R1 and a capacitor C1 and is connected to the second electrode 7 through a resistor R2 and a capacitor C2. When the ring is worn, the signal excitation module 9 is coupled to the body tissue through the first electrode 6 and the second electrode 7, so that alternating voltage signals with the same frequency are generated. The alternating voltage signals are collected and demodulated by the signal processing module 10 by alternating current coupling. Specifically, the signals collected by the first electrode 6 and the second electrode 7 are inputted to a band-pass filter module 11 through two sampling capacitors C3 and C4 respectively, low-pass filtering is performed on the band-pass filtered signals by a low-pass filter 12, and the filtered signals are transmitted to the microprocessor module 1.

In this embodiment, the first electrode 6 and the first electrode 7 are used to generate an excitation signal as well as collect a signal, which reduces the number of electrodes for skin conductance monitoring to two. In addition, because the electrocardiographic monitoring analog front end 3 is connected to the first electrode 6 and the second electrode 7 by direct current coupling, and the skin conductance monitoring module 4 is connected to the first electrode 6 and the second electrode 7 by alternating current coupling, the electrocardiographic signal and the skin impedance signal collected by the first electrode 6 and the second electrode 7 will not interfere with each other. It should be noted that the electrocardiographic monitoring analog front end 3 may be connected to the first electrode 6 and the second electrode 7 by alternating current coupling, while the skin conductance monitoring module 4 may be connected to the first electrode 6 and the second electrode 7 by direct current coupling.

Figure 4:
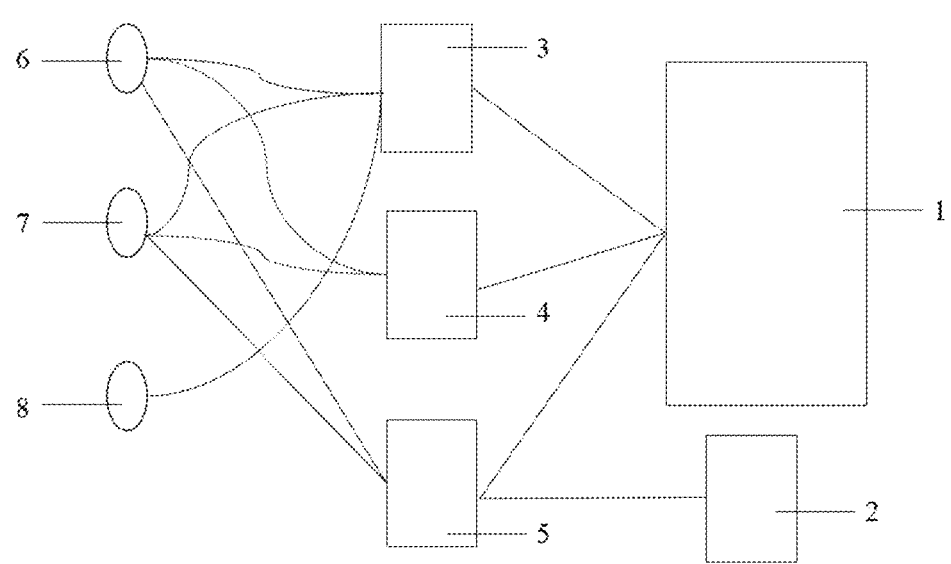
FIG. 4 is another schematic diagram of function modules of an electrode multiplexing physiological parameter monitoring ring according to an embodiment of the present invention.

FIG. 4 is a schematic diagram of another function module of an electrode multiplexing physiological parameter monitoring ring according to an embodiment of the present invention. As shown in FIG. 4, to further multiplex the electrodes, according to an embodiment of the present invention, the electrode multiplexing physiological parameter monitoring ring may further include a power supply management module 5 connected to the microprocessor module 1. The first electrode 6 and the second electrode 7 are separately connected to a built-in power supply 2 through the power supply management module 5. The power supply management module 5 is configured to: when the first electrode 6 and the second electrode 7 are in contact with the skin, from an open circuit between the first electrode 6 and the built-in power supply 2; and when the first electrode 6 and the second electrode 7 are connected to an external charger, form a closed-circuit between the first electrode 6 and the built-in power supply 2. The microprocessor module is configured to: when the closed-circuit is formed between the first electrode 6 and the built-in power supply 2, make the electrocardiogram monitoring analog front end 3 and the skin conductance monitoring module 4 stop working. In this embodiment, the first electrode 6, the second electrode 7, the power supply management module 5, and the built-in power supply 2 constitute a charging structure, and the first electrode 6 and the second electrode 7 are used as charging interfaces to charge the built-in power supply 2. According to this embodiment, the physiological parameter monitoring ring can implement the electrocardiogram monitoring, the heart rate monitoring, the skin conductance monitoring, and a charging function by multiplexing the first electrode 6 and the second electrode 7, so that the number of electrodes can be further reduced, system design can be simplified, and the device can be further miniaturized. In addition, according to this embodiment, the physiological parameter monitoring function and the charging function of the physiological parameter monitoring ring can be automatically switched, so that system complexity is further reduced, and lower power consumption is implemented.

The microprocessor module 1 may be connected to the power supply management module 5 through an IO interface.

Figure 5:
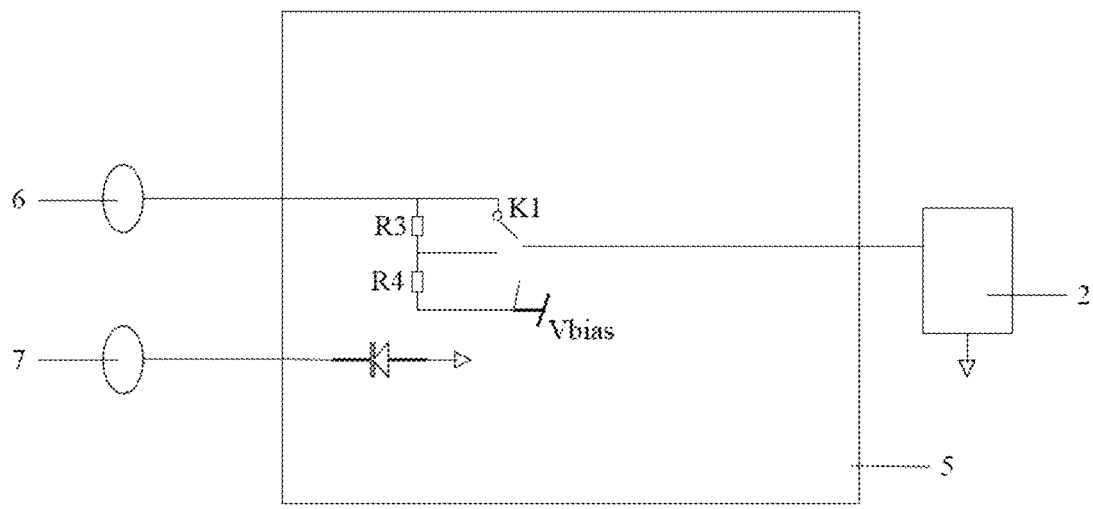
FIG. 5 is a schematic circuit diagram of a power supply management module of an electrode multiplexing physiological parameter monitoring ring according to an embodiment of the present invention.

Preferably, as shown in FIG. 5, the power supply management module 5 includes resistors R3 and R4, a bias voltage Vbias of the system, and a voltage control switch K1. The bias voltage Vbias is connected to the first electrode 6 through the resistors R3 and R4. The Vbias voltage is greater than 2V and less than 3.3V. The voltage control switch K1 is used for controlling the first electrode 6 to connect to a connection point of the resistors R3 and R4 or connect to one pole of the built-in power supply 2. In a physiological parameter monitoring mode, the voltage difference between the body surface electrodes is at an mV level. Therefore, the voltage on the first electrode 6 is smaller than the Vbias voltage, the voltage control switch K1 connects the first electrode 6 and the connection point of the resistors R3 and R4, there is an open circuit between the first electrode 6 and the built-in power supply 2, and the built-in power supply 2 is not charged. When the ring is connected to the external charger, the voltage on the first electrode 6 is larger than the Vbias voltage, the voltage control switch K1 connects the first electrode 6 to one pole of the built-in power supply 2, there is a closed-circuit between the first electrode 6 and the built-in power supply 2, and the built-in power supply 2 is charged. At the same time, the microprocessor module 1 controls, by an analog switch, the power supply of the electrocardiogram monitoring analog front end 3 and the skin conductance monitoring module 4 to be turned off, so as to make the physiological parameter monitoring module stop working. In this embodiment, the switching between the physiological parameter monitoring function and the charging function is automatically controlled by the voltage control switch K1, so that the built-in power supply is not charged when the physiological parameter detection is performed, and the physiological parameter monitoring is not performed when the built-in power supply is charged, and the two functions do not affect each other.

It should be noted that, in the claims and the descriptions of the present patent, relational terms "first", "second", and the like are only used to distinguish one entity or operation from another entity or operation, but are not intended to indicate any actual relationship or order between entities or operations. Moreover, the terms "include", "have", and any other variants thereof are intended to cover non-exclusive inclusion, so that a process, a method, article, or a device that includes a series of elements not only includes those elements, but includes other elements that are not clearly listed or are inherent to the process, the method, the article, or the device. Without more restrictions, an element that is defined by the phrase "including a" does not exclude the presence of another same element in the process, method, article, or device that includes the element.

Although the present invention has been illustrated and described with reference to the preferred embodiments of the present invention, it should be understood by persons of ordinary skills in the art that various changes in form and details may be made without departing from the spirit and scope of the present invention.

The invention claimed is:

1. An electrode multiplexing physiological parameter monitoring ring, comprising a built-in power supply, a microprocessor module, an electrocardiogram monitoring analog front end, a skin conductance monitoring module, a first electrode, and a second electrode, the microprocessor module is connected to the electrocardiogram monitoring analog front end and the skin conductance monitoring module, wherein the first electrode and the second electrode are separately connected to the electrocardiogram monitoring analog front end, and the electrocardiogram monitoring analog front end processes electrocardiogram signals collected by the first electrode and the second electrode;

the first electrode and the second electrode are further separately connected to the skin conductance monitoring module, and the skin conductance monitoring module processes skin impedance signals collected by the first electrode and the second electrode; and a coupling manner in which the first electrode and the second electrode are coupled to the electrocardiogram monitoring analog front end is direct current coupling or alternating current coupling, and is opposite to a coupling manner in which the first electrode and the second electrode are coupled to the skin conductance monitoring module;

wherein the electrocardiographic monitoring analog front end is connected to the first electrode and the second electrode by direct current coupling, and the skin conductance monitoring module is connected to the first electrode and the second electrode by alternating current coupling, or the electrocardiographic monitoring analog front end may be connected to the first electrode and the second electrode by alternating current coupling, while the skin conductance monitoring module may be connected to the first electrode and the second electrode by direct current coupling, so that the electrocardiographic signal and the skin impedance signal collected by the first electrode and the second electrode will not interfere with each other wherein the ring further comprises a power supply management module connected to the microprocessor module, and the first electrode and the second electrode are separately connected to the built-in power supply through the power supply management module;

the power supply management module is configured to: when the first electrode and the second electrode are in contact with skin, form an open circuit between the first electrode and the built-in power supply, and when the first electrode and the second electrode are connected to an external charger, form a closed-circuit between the first electrode and the built-in power supply; and the microprocessor module is configured to: when the closed-circuit is formed between the first electrode and the built-in power supply, make the electrocardiogram monitoring analog front end and the skin conductance monitoring module stop working, and wherein the power supply management module comprises a third resistor, a fourth resistor, a bias voltage, and a voltage control switch, one end of the third resistor is connected to the first electrode and the voltage control switch, the other end of the third resistor is connected to the fourth resistor, and the other end of the fourth resistor is connected to the bias voltage; when the first electrode is in contact with the skin, the other end of the voltage control switch is connected to a connection point of the third resistor and the fourth resistor; and when the first electrode is connected to the external charger, the other end of the voltage control switch is connected to the built-in power supply.

2. The electrode multiplexing physiological parameter monitoring ring according to claim 1, wherein the ring further comprises a third electrode connected to the electrocardiogram monitoring analog front end, the electrocardiogram monitoring analog front end processes electrocardiogram signals collected by the first electrode, the second electrode, and the third electrode, and the third electrode is coupled to the electrocardiogram monitoring analog front end in a manner of direct current coupling.

3. The electrode multiplexing physiological parameter monitoring ring according to claim 1, wherein the skin conductance monitoring module comprises a signal excitation module and a signal processing module.

4. The electrode multiplexing physiological parameter monitoring ring according to claim 3, wherein the signal excitation module comprises a current source, a first resistor, a second resistor, a first capacitor, and a second capacitor, one end of the first resistor is connected to the current source, the other end of the first resistor is connected to the first capacitor, and the other end of the first capacitor is connected to the first electrode; and one end of the second resistor is connected to the current source, and the other end of the second resistor is connected to the second capacitor, and the other end of the second capacitor is connected to the second electrode.

5. The electrode multiplexing physiological parameter monitoring ring according to claim 3, wherein the signal excitation module generates an alternating current with a frequency higher than 32 kHz and amplitude lower than 100 µA.

6. The electrode multiplexing physiological parameter monitoring ring according to claim 3, wherein the signal processing module comprises a third capacitor, a fourth capacitor, a band-pass filter and a low-pass filter, one end of the third capacitor is connected to the first electrode, the other end of the third capacitor is connected to the band-pass filter, and the other end of the band-pass filter is connected to the low-pass filter; and one end of the fourth capacitor is connected to the second electrode, and the other end of the fourth capacitor is connected to the band-pass filter.

7. The electrode multiplexing physiological parameter monitoring ring according to claim 1, wherein the bias voltage is greater than 2V and less than 3.3 V.

* * * * *